United States Patent
Brooks et al.

(10) Patent No.: US 9,643,867 B2
(45) Date of Patent: May 9, 2017

(54) WASTE PROCESSING SYSTEM WITH ANAEROBIC MECHANISM AND METHOD OF OPERATION THEREOF

(71) Applicant: BIOVESSEL TECHNOLOGIES INC., Vancouver, OT (CA)

(72) Inventors: Jeff Brooks, Vancouver (CA); Chaiyos Siripoke, San Jose, CA (US)

(73) Assignee: Biovessel Technologies Inc., Vancouver (CA)

( * ) Notice: Subject to any disclaimer, the term of this patent is extended or adjusted under 35 U.S.C. 154(b) by 126 days.

(21) Appl. No.: 14/313,936

(22) Filed: Jun. 24, 2014

(65) Prior Publication Data

US 2015/0076058 A1    Mar. 19, 2015

Related U.S. Application Data

(60) Provisional application No. 61/838,546, filed on Jun. 24, 2013.

(51) Int. Cl.
*C02F 3/28* (2006.01)
*C02F 11/04* (2006.01)
(Continued)

(52) U.S. Cl.
CPC .............. *C02F 3/284* (2013.01); *C02F 3/006* (2013.01); *C02F 3/2866* (2013.01); *C02F 11/04* (2013.01); *C12M 21/04* (2013.01); *C12M 27/20* (2013.01); *C12M 41/22* (2013.01); *C12M 45/02* (2013.01); *C02F 3/301* (2013.01); *C02F 3/348* (2013.01);
(Continued)

(58) Field of Classification Search
CPC .......... C02F 3/284; C02F 3/006; C02F 3/301; C02F 3/348; C02F 11/04; C02F 2103/20; C02F 2209/005; C02F 2209/02; C02F 2209/03; C02F 2209/06; C02F 2209/38; C02F 2209/40; C02F 2209/42; C02F 2301/106; C02F 2303/12; C02F 2305/06; C02F 2203/006; C02F 3/2866; C12M 21/04; C12M 27/20; C12M 41/22; C12M 45/02; Y02W 10/23; Y02E 50/343
USPC ....... 210/603, 612, 613, 614, 173, 175, 252, 210/259
See application file for complete search history.

(56) References Cited

U.S. PATENT DOCUMENTS 8,221,626 B2    7/2012   Sassow
8,522,435 B2    9/2013   Sassow
(Continued)

FOREIGN PATENT DOCUMENTS

KR    1020110055442 A    5/2011
WO    WO 2013/069026 A1 *    5/2013

*Primary Examiner* — Fred Prince
(74) *Attorney, Agent, or Firm* — Smiths IP

(57) ABSTRACT

A waste processing system includes: an input module for converting input organic waste into processed input waste; a digester module, coupled to the input module, for generating biogas and digester effluent from the processed input waste, including: a digester tank; baffles affixed within the digester tank; a digester process solution in the digester tank including, hydrolytic bacteria, acidogenic bacteria, acetogenic bacteria, methanogenic bacteria, or a combination thereof, for converting the processed input waste into the biogas and the digester effluent; and an output module, coupled to the digester module, for collecting the biogas and digester effluent after a residence period.

6 Claims, 9 Drawing Sheets

(51) Int. Cl.
*C02F 3/30* (2006.01)
*C02F 3/34* (2006.01)
*C12M 1/107* (2006.01)
*C02F 3/00* (2006.01)
*C12M 1/00* (2006.01)
*C12M 1/02* (2006.01)
*C12M 1/33* (2006.01)
*C02F 103/20* (2006.01)

(52) U.S. Cl.
CPC .... *C02F 2103/20* (2013.01); *C02F 2203/006* (2013.01); *C02F 2209/005* (2013.01); *C02F 2209/02* (2013.01); *C02F 2209/03* (2013.01); *C02F 2209/06* (2013.01); *C02F 2209/38* (2013.01); *C02F 2209/40* (2013.01); *C02F 2209/42* (2013.01); *C02F 2301/106* (2013.01); *C02F 2303/12* (2013.01); *C02F 2305/06* (2013.01); *Y02E 50/343* (2013.01); *Y02W 10/23* (2015.05)

(56) References Cited

U.S. PATENT DOCUMENTS

| | | |
|---|---|---|
| 2008/0223783 A1 | 9/2008 | Sutton |
| 2009/0227003 A1* | 9/2009 | Blotsky .............. C12M 21/02 435/257.1 |
| 2010/0105127 A1 | 4/2010 | Ginsburg |
| 2010/0155313 A1 | 6/2010 | Wilson et al. |
| 2012/0261337 A1 | 10/2012 | Weiss |

* cited by examiner

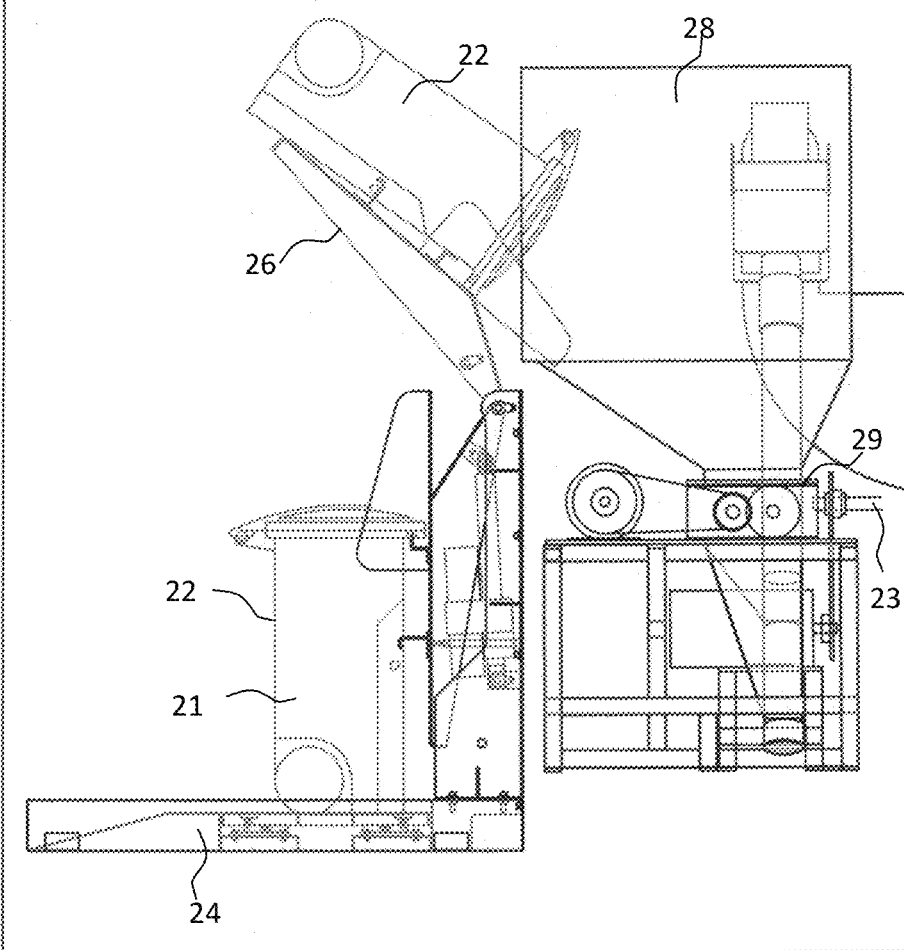

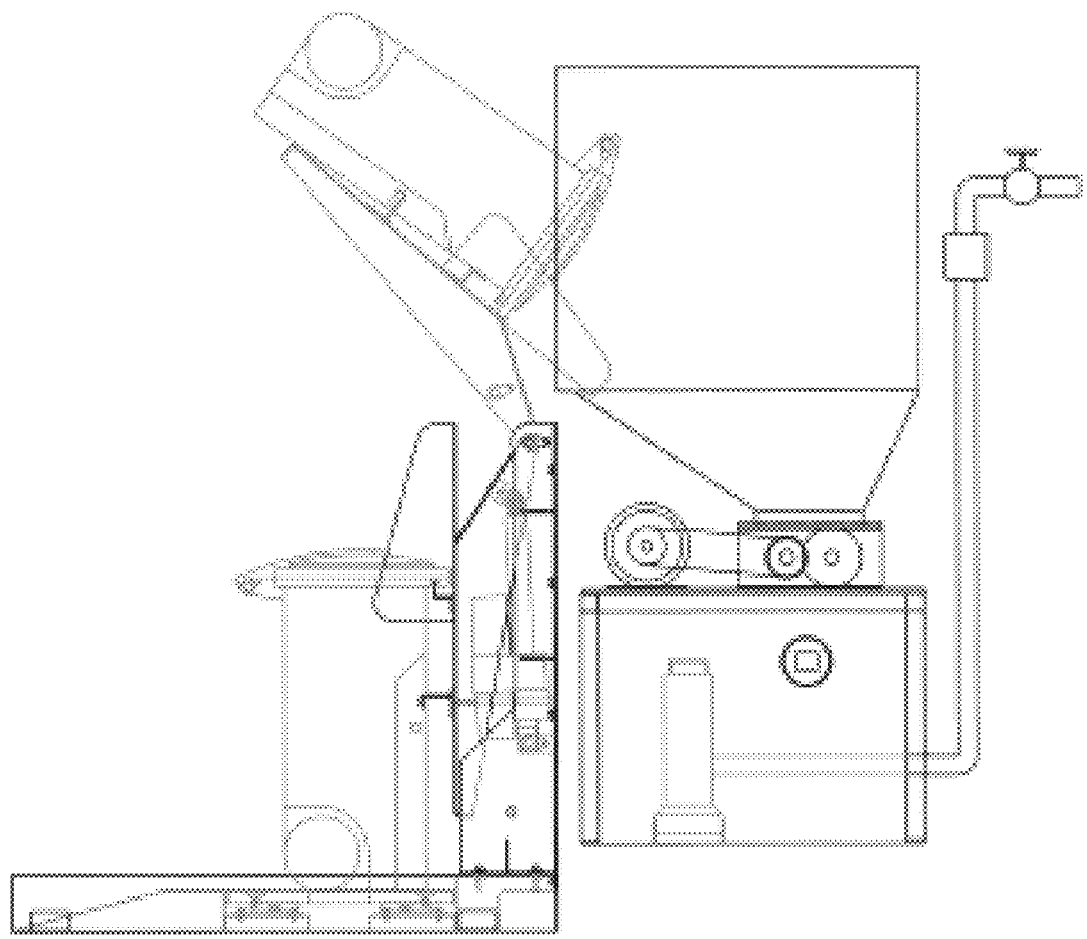

SCALE
PART OF INPUT ASSEMBLY

MOTORIZED LIFT MECHANISM
PART OF INPUT ASSEMBLY

DELIVERY HOPPER AND GRINDER ASSEMBLY
PART OF INPUT ASSEMBLY

DELIVERY HOPPER AND GRINDER ASSEMBLY
PART OF INPUT ASSEMBLY

ORGANIC WAST DELIVERY ASSEMBLY
PART OF INPUT ASSEMBLY

AUGER ASSEMBLY
PART OF INPUT ASSEMBLY

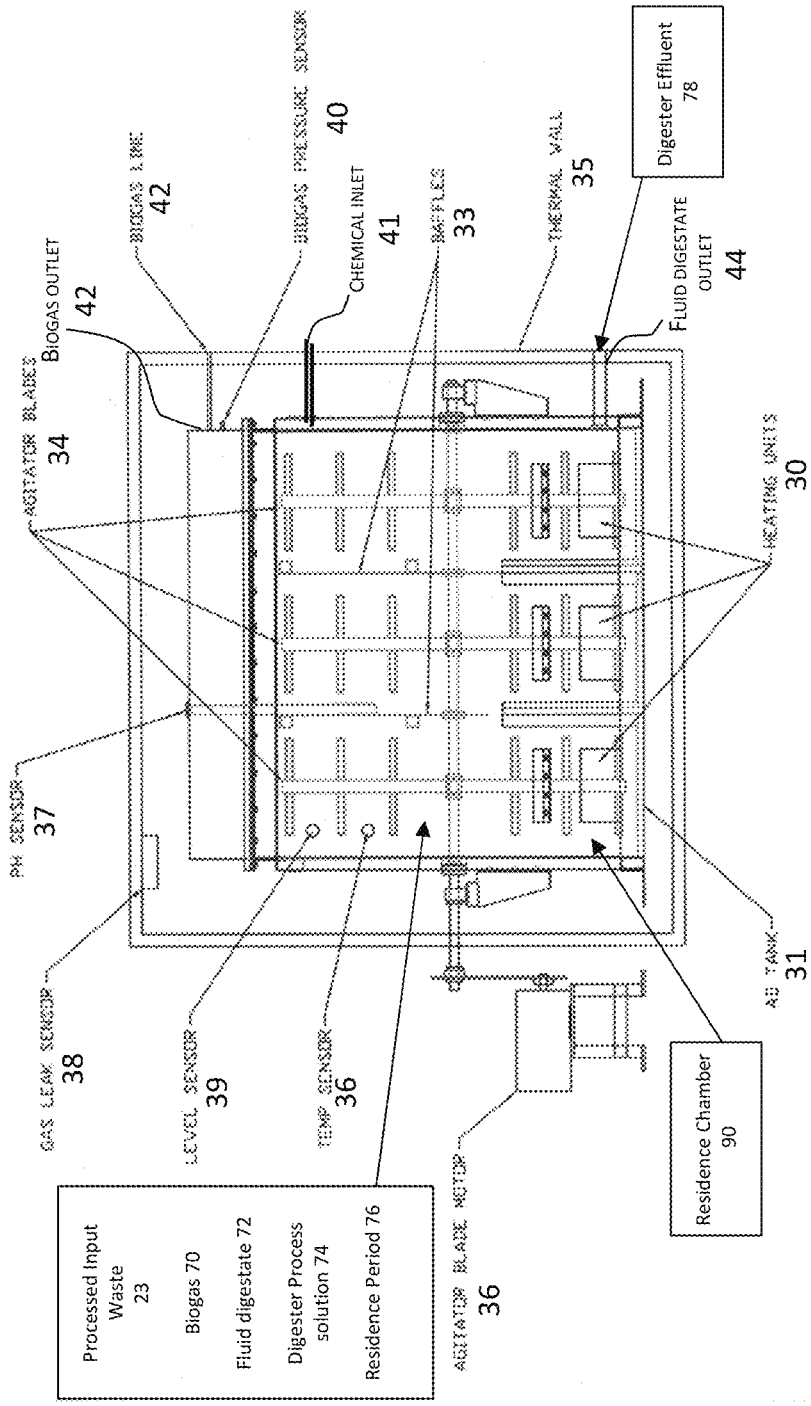

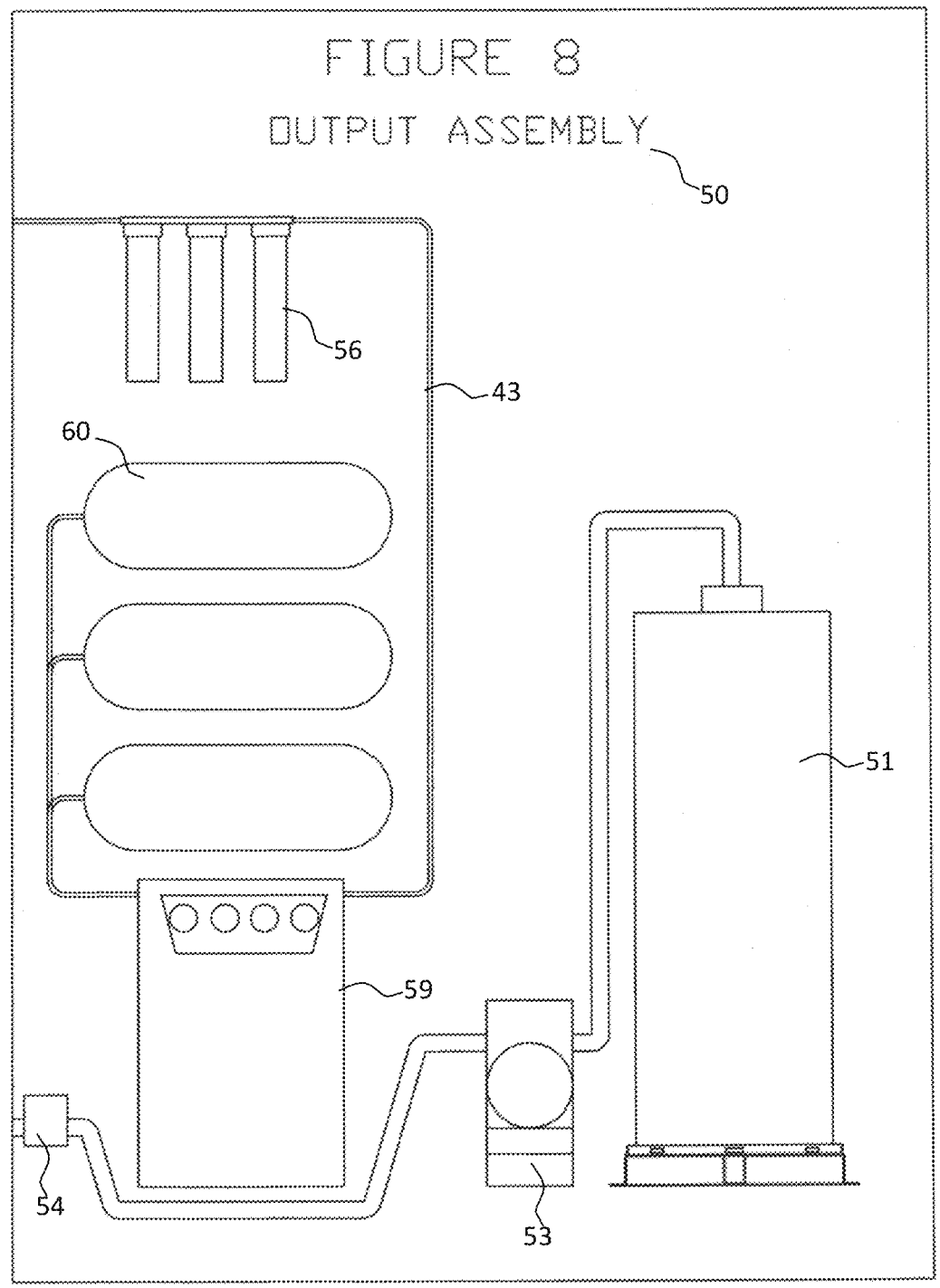

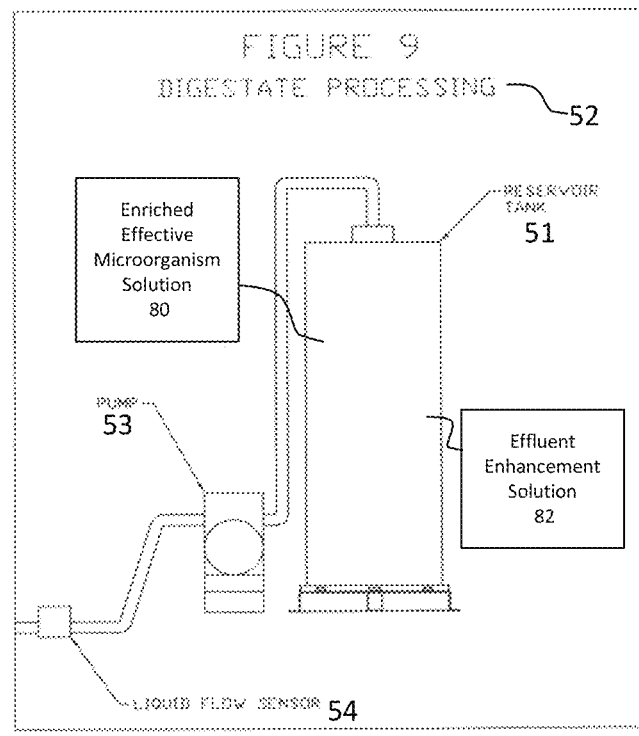
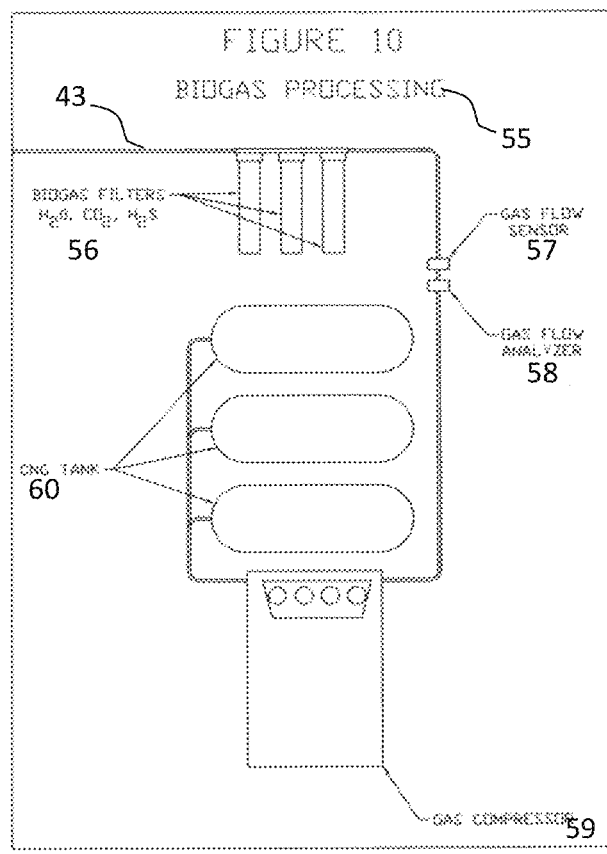

WASTE PROCESSING SYSTEM WITH ANAEROBIC MECHANISM AND METHOD OF OPERATION THEREOF

CROSS-REFERENCE TO RELATED APPLICATION(S)

This application claims the benefit of U.S. Provisional Patent Application Ser. No. 61/838,546 filed Jun. 24, 2013, and the subject matter thereof is incorporated herein by reference thereto.

TECHNICAL FIELD

An embodiment of the present invention relates generally to a waste processing system, and more particularly to a system for anaerobic digestion of organic waste.

BACKGROUND

Organic waste material, such as municipal wastewater or livestock manure, can present problems when generated on a large scale. Organic waste material can be a health risk and a nuisance. The disposal of Organic Food Resource Material is normally collected from the point of generation, hauled to a landfill and dumped without any further processing to harvest the resources contained within the material. It is well documented that the off-gas from this material in the forms of $CO_2$, $H_2S$ and $CH_4$ has significant and harmful effects upon the environment. All waste at a landfill is processed with vehicles that utilize some form of fuel adding to the carbon footprint when processing. Traditional composting is not always feasible due to the commercial locations or sea faring vessels. Composting has been initiated at numerous landfill facilities. It is a lengthy process requiring a strict protocol to maintain the proper decomposition parameters without odors and requires energy intensive specialized motor vehicles and machines to maintain the process. Additionally, removal of off gassing of $CO_2$, $H_2S$ and $CH_4$ can also poses a problem. Climate and location can provide challenges, particularly in climates of extreme cold and heat. With many large-scale generators of significant quantities of food waste, on-site location for processing the OFRM is required. Additionally, vermin and scavenger animals and other obstacles can become an immediate problem associated with compost storage.

Decomposing organic waste can also release greenhouse gases, such as methane and carbon dioxide, as well as hydrogen sulfide which is the odorous smell associated with rotting garbage and thus can lead to a source of air and water pollution. Strategies for dealing with organic waste in large quantities are therefore needed. Organic waste material can be converted into useful products or can have useful products extracted from it. This conversion can be done within waste conversion facilities, such as, for example, an anaerobic bio-digester. Anaerobic bio-digesters generally process the organic material by treatment with organisms, which can be obligate or facultative anaerobic bacteria. These organisms can, using biochemical reactions, convert organic material into a variety of products. Among these products are a mixture of gases, generally referred to as biogas, and a mixture of liquids and solids, generally referred to as biodigestate.

Biogas can include methane, carbon dioxide, and amounts of other gases. Biogas can be burned to provide electricity locally, and can also be transferred to utility companies or transmission networks as natural gas. However, biogas from an anaerobic bio-digester can contain impurities that must be removed before transmission to utility companies. These impurities, which can include carbon dioxide and hydrogen sulfide can be harmful to the environment and are generally disposed of as waste products.

Concerns about overuse of fossil fuels, based in part on environmental concerns and their substantially non-renewable nature, have generated interest in biological sources of energy. Biological energy sources can be desirable because the processes used to produce or extract them are generally less damaging to the environment. Biological energy sources can also be renewable because they are generally derived from plant and/or animal material.

Bio-production facilities can use biological organisms and processes to generate useful products, including biological energy sources, from raw materials. Examples of such bio-production facilities include ethanol plants and bio-diesel plants, where organisms, such as yeasts or algae use biochemical processes to generate from a feedstock, products that can be useful, such as ethanol or triglycerides, respectively.

However, one common problem of stand-alone waste conversion facilities and bio-production facilities is that they use products that must be acquired from external sources. These products include feedstock for the bio-production facilities, and organic material for waste conversion facilities. Importing products from external sources can cause loss of efficiency and can incur significant expenses on the operation of these facilities.

Anaerobic digestion of biological waste to produce bio-fuels is a growing area of interest as concerns about greenhouse gas emissions grow and the use of, and demand for, alternative and renewable energy sources increases. This form of digestion is the process in which an environment free of oxygen allows certain microorganisms to flourish, consuming biological solids and creating biogas that contains a considerable amount of methane. If not collected, the bio-gas enters the atmosphere as a greenhouse gas with a much stronger greenhouse effect than carbon dioxide. If captured, the biogas can be used to generate heat and/or electricity and/or can be used to eliminate solid wastes. There are a number of limitations in the current implementations of the anaerobic digestion technology. In particular, anaerobic digestion is sensitive to temperature, and if the temperature of the biological solids is too low, then the digestion process will either slow or even halt completely. Slower digestion times require longer retention times that lead to higher costs due to increased digestion tank size. Many anaerobic digestion systems utilize much of the energy produced by the system in the form of heat just to maintain digester temperature and digester function. These temperature requirements normally limit the areas where anaerobic digestion is feasible to a warmer, more temperature stable environment.

In view of the foregoing, it would be desirable to provide a system that reduces the need to dispose of by-products and waste products generated in waste conversion facilities, bio-production facilities, and other facilities. Accordingly, there is a need for alternatives to the traditional composting methods to address these issues. Solutions to these problems have been long sought but prior developments have not taught or suggested any solutions and, thus, solutions to these problems have long eluded those skilled in the art.

SUMMARY

An embodiment of the present invention provides a system, including: an input module for converting input organic waste into processed input waste; a digester module, coupled to the input module, for generating biogas and digestate effluent from the processed input waste, including: a digester tank; baffles affixed within the digester tank; a digester process solution in the digester tank including, hydrolytic bacteria, acidogenic bacteria, acetogenic bacteria, methanogenic bacteria, or a combination thereof, for converting the processed input waste into the biogas and the digestate effluent; and an output module, coupled to the digester module, for collecting the biogas and digester effluent after a residence time.

An embodiment of the present invention provides a system, including: an input module for converting input organic waste into processed input waste; a digester module, coupled to the input module, for generating biogas and digestate effluent from the processed input waste, including: a digester tank; baffles affixed within the digester tank; a digester process solution in the digester tank including, hydrolytic bacteria, acidogenic bacteria, acetogenic bacteria, methanogenic bacteria, or a combination thereof, for converting the processed input waste into the biogas and the digestate effluent; an output module, coupled to the digester module, for collecting the biogas and digester effluent after a residence time; and an distillate fluid processing apparatus, coupled to the output module, for processing the digester effluent with an effluent enhancement solution to generate an enriched effective microorganism solution An embodiment of the present invention provides a method including: processing input organic waste to generate processed input waste; combining the processed input waste with a digester process solution in a digester module to generate biogas and fluid digestate, the digester process solution includes hydrolytic bacteria, acidogenic bacteria, acetogenic bacteria, methanogenic bacteria, or a combination thereof; collecting the biogas; and generating digester effluent at a solids content of about 10% from the fluid digestate based on a residence period.

Certain embodiments of the invention have other steps or elements in addition to or in place of those mentioned above. The steps or elements will become apparent to those skilled in the art from a reading of the following detailed description when taken with reference to the accompanying drawings.

BRIEF DESCRIPTION OF THE DRAWINGS

FIGS. 2A and 2B are schematic representations of the input module.

FIG. 7 is a schematic representation of one embodiment of the digester module.

FIG. 8 is a schematic representation of the output module.

FIG. 9 is a schematic representation of an embodiment of the distillate fluid processing apparatus.

FIG. 10 is a schematic view of an embodiment of the biogas processing apparatus.

DETAILED DESCRIPTION

Figure 1:
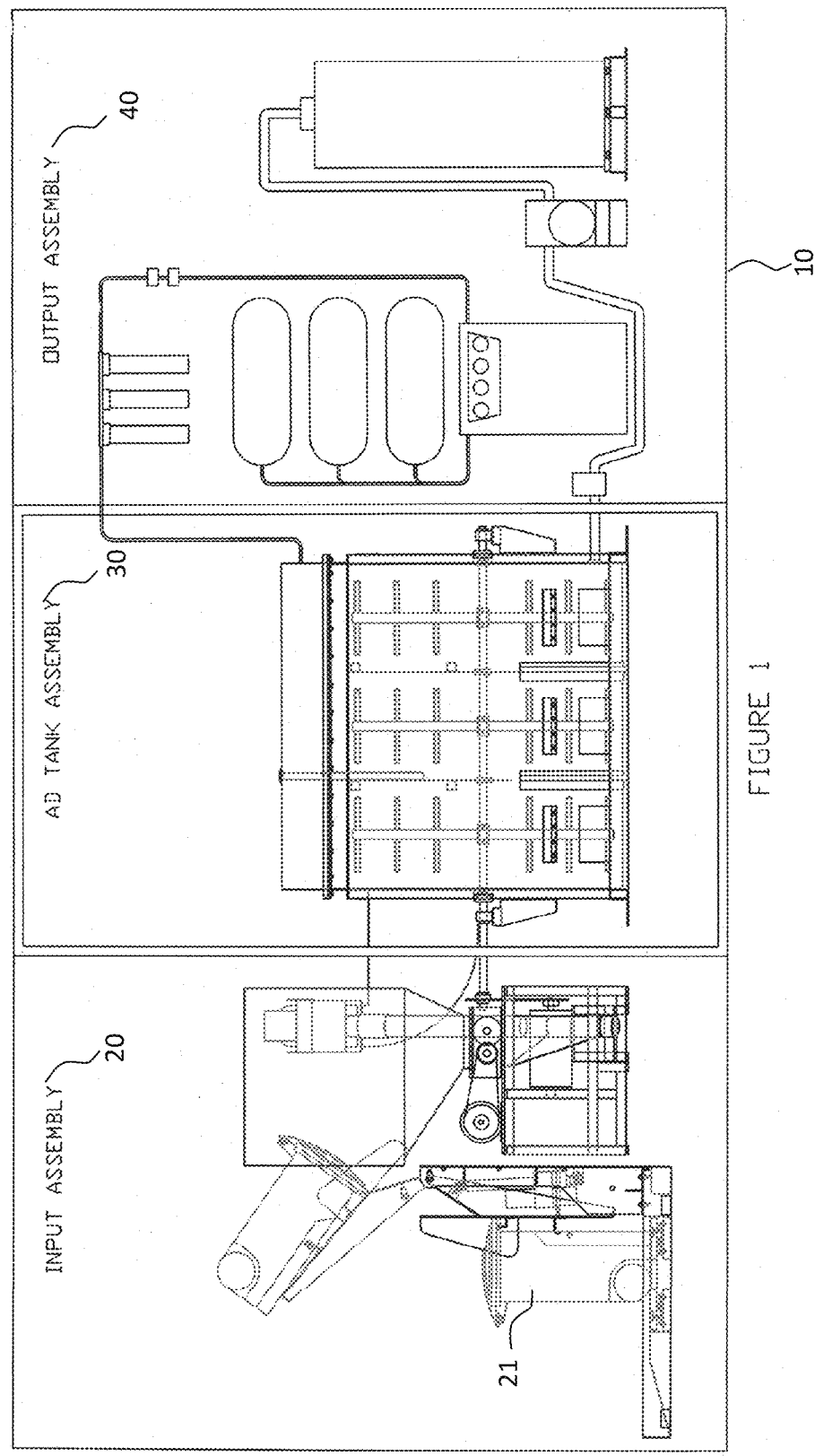
FIG. 1 is a schematic representation of an apparatus of A Biovessel bio-digester.

The present invention generally relates to systems, method and apparatus, for complete conversion of organic waste to energy or other useful biofuels. One aspect relates to an apparatus for complete digestion of organic waste to renewable energy, the apparatus herein referred to as a "BioVessel" which converts biodegradable material into a biogas for a renewable energy source and/or a fluid digestate which can be utilized as a fertilizer, soil amendment or conditioner or for other uses, for example, converted to a high quality micronutrient or Effective Microorganism. The BioVessel bio-digester as disclosed herein comprises three modular sections, including an input module, a digester module and an output module.

The following embodiments are described in sufficient detail to enable those skilled in the art to make and use the invention. It is to be understood that other embodiments would be evident based on the present disclosure, and that system, process, or mechanical changes may be made without departing from the scope of an embodiment of the present invention.

In the following description, numerous specific details are given to provide a thorough understanding of the invention. However, it will be apparent that the invention may be practiced without these specific details. In order to avoid obscuring an embodiment of the present invention, some well-known circuits, system configurations, and process steps are not disclosed in detail.

The drawings showing embodiments of the system are semi-diagrammatic, and not to scale and, particularly, some of the dimensions are for the clarity of presentation and are shown exaggerated in the drawing figures. Similarly, although the views in the drawings for ease of description generally show similar orientations, this depiction in the figures is arbitrary for the most part. Generally, the invention can be operated in any orientation. The embodiments have been numbered first embodiment, second embodiment, etc. as a matter of descriptive convenience and are not intended to have any other significance or provide limitations for an embodiment of the present invention.

For convenience, certain terms employed in the entire application are collected here. Unless defined otherwise, all technical and scientific terms used herein have the same meaning as commonly understood by one of ordinary skill in the art to which this invention belongs.

The terms "lower", "reduced", "reduction" or "decrease" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease, or any decrease between 10-100% as compared to a reference level.

The terms "increased", "increase" or "enhance" or "higher" are all used herein to generally mean an increase by a statically significant amount; for the avoidance of any doubt, the terms "increased", "increase" or "enhance" or "higher" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "substantially pure", with respect to a biogas, refers to a biogas that is at least about 75%, preferably at least about 85%, more preferably at least about 90%, and most preferably at least about 95% pure, with respect to gas molecules making up the biogas. Recast, the terms "substantially pure" or "essentially purified", with regard to a biogas, refers to a biogas that contain fewer than about 20%, more preferably fewer than about 15%, 10%, 8%, 7%, most preferably fewer than about 5%, 4%, 3%, 2%, 1%, or less than 1%, of molecules which are not of the desired biogas.

The term "computer" can refer to any non-human apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" may refer to any storage device used for storing data accessible by a computer, as well as any other means for providing access to data by a computer. Examples of a storage-device-type computer-readable medium include: a magnetic hard disk; a floppy disk; an optical disk, such as a CD-ROM and a DVD; a magnetic tape; a memory chip.

The term "software" is used interchangeably herein with "program" and refers to prescribed rules to operate a computer. Examples of software include: software; code segments; instructions; computer programs; and programmed logic.

The term a "computer system" may refer to a system having a computer, where the computer comprises a computer-readable medium embodying software to operate the computer.

As used herein the term "comprising" or "comprises" is used in reference to compositions, methods, and respective component(s) thereof, that are essential to the invention, yet open to the inclusion of unspecified elements, whether essential or not. By way of further example, a composition that comprises elements A and B also encompasses a composition consisting of A, B and C. The terms "comprising" means "including principally, but not necessary solely". Furthermore, variation of the word "comprising", such as "comprise" and "comprises", have correspondingly varied meanings. The term "consisting essentially" means "including principally, but not necessary solely at least one", and as such, is intended to mean a "selection of one or more, and in any combination." In the context of the specification, the term "comprising" means "including principally, but not necessary solely". Furthermore, variation of the word "comprising", such as "comprise" and "comprises", have correspondingly varied meanings.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean±1%. The present invention is further explained in detail by the following, including the Examples, but the scope of the invention should not be limited thereto.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

This invention is further illustrated by the following examples which should not be construed as limiting. The contents of all references cited throughout this application, as well as the figures and tables are incorporated herein by reference.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Referring now to FIG. 1, therein is shown a schematic representation of an apparatus of A Biovessel bio-digester 10. The Biovessel 10 can include three modular sections for anaerobic digestion of input organic waste 21, such as Organic Food Resource Material, an input module 20, Digester module 30, and an output module 50. It is understood that "Organic Food Resource Material" can be used interchangeably with the input organic waste 21 unless otherwise specified below.

The Biovessel 10 can be a complete standalone anaerobic digester system. The Biovessel 10 can include a number of features, which are briefly mentioned herein and discussed in greater detail below. As an example, the Biovessel 10 can include a firewalled enclosure and electronic thermal controls to maintain consistent temperature in all climates. In some embodiments, the Biovessel 10 can be wrapped in steel cladding allowing for indoor and outdoor installations.

In some embodiments, the Biovessel 10 can utilize an array of sensors to monitor all processes throughout the machine. For example, the types of data collected range from the input organic waste 21, output of biogas to the health of the microbes inside the digester module 30. Data is recorded and processed by an onboard CPU and made available for secure download via Ethernet or WiFi.

As described in greater detail below, the present invention is tailored to comprise a specific microbiom. The BioVessel 10 is an alternative to traditional composting and addresses problems such as need to remove waste byproducts from the composting, e.g., gasses such as $CO_2$ and $H_4S$ as well as the end digested product. While similar appearing technologies have been developed to meet the problems of organic food wastes, these systems, unlike the BioVessel 10 technology as disclosed herein, do not close the loop completely and do not extract the maximal amount of value from the OFRM.

For example, other systems or digesters discard the effluent down the sewer line which can lead to pollution and/or are dealt with by the municipalities, while other systems and digesters require additional time for the composing of the OFRM. In some cases, other available systems and digesters use the semi-processed effluent material as a soil amendment, which poses a hazard of mold growth. Accordingly, none of the current systems or digesters are able to capture the gas for cleaning and utilization as a clean fuel source.

In contrast, the BioVessel 10 as disclosed herein digests the OFRM into useful biogases, e.g., methane, a solid and a fluid digestate liquid, which are used as beneficial and marketable soil products. Accordingly, the present bio-digester as disclosed herein provides a significant advantage over other bio-digesters in that it extracts all the value from the OFRM and closes the loop, and does not result in any unusable waste.

Additionally, the advantages of the BioVessel 10 system and processes as disclosed herein are not limited to energy output of the system. The system provides a significant reduction of volume in the waste solids thereby reducing the costs associated with disposal and/or distribution. For example, the biogas, e.g., methane produced from the anaerobic digestion of the OFRM using the systems, methods and devices as disclosed herein can be readily compressed to produce an enriched compressed natural gas having 95% less emissions per Gallon Gasoline Equivalent than diesel fuel or alternatively can be sold to a gas pipeline utility or for use in the transportation industry or other uses. The digester effluent produced from the anaerobic digestion of the OFRM using the systems, methods and devices as disclosed herein can be used as a pathogen free digestate which can be utilized as a fertilizer, soil amendment or conditioner or for other uses, for example, it can be converted in proprietary manor to a high quality micronutrient or Effective Microorganism. An additional advantage is that the BioVessel 10 system as disclosed herein is a small unit, which can be scaled appropriately to the space available, and does not require the large space requirements of other digesters.

Alternatively, the biogases and/or fluid digestate created by the BioVessel 10 system can be used in conjunction with an electricity generator such as a fuel cell or internal combustion engine, combustion turbine or the like connected to an electrical generator to produce electricity that can be fed to the grid. The flexibility of the output of the process of the present invention allows the system to offset electricity and heating costs for the digestion or other operations in the facility while simultaneously producing a product as disclosed herein) which can be sold to further offset costs and/or generate profit.

The BioVessel 10 system as disclosed herein are suitable for use in any business, municipal or school campus with cafeterias, food processing facilities of any size, supermarkets, restaurants, hospitals, hotels, seasonal open-air markets, sporting events, cruise ships or other ships, and anywhere there is an abundance of organic food waste can effectively utilize the BioVessel 10 system technology.

Accordingly, the BioVessel 10 system as disclosed herein closes-the-loop of OFRM, in a quiet and efficient manner. It eliminates odor and vermin problems, uses minimal power and water and eliminates harmful greenhouse gases. The bio-digester of the BioVessel 10 system as disclosed herein digests organic waste into an energy source and delivers a pathogen free digestate that is utilized as a fertilizer, soil amendment or conditioner. Accordingly, the bio-digester as disclosed herein eliminates the need to process or dispose of the organic waste further by closing-the-loop in the ideal and most healthful organic waste management system available to date. All other fees associated with dealing with the removal of the organic waste or the nuisance involved with onsite storage of waste products and their removal are therefore eliminated.

Further, the present invention relates to a device, apparatus and method for a high-moisture fermentation process using a microbial ecological selection signature process utilizing a specific bacterial component comprising methanogenic bacteria within the BioVessel 10 system that releases the nutritional and energy elements of the OFRM.

Referring now to FIG. 2A and FIG. 2B, therein is shown schematic representations of the input module 20. The input module 10 can include an auger 27 or a pump/injector 45 to deliver processed input waste 23 to the digester module 30 of FIG. 1. The processed input waste 23 is input waste, such as the OFRM of the input organic waste 21, that has been processed to reduce the particle size of the solid components, contaminants, impurities, or a combination thereof in the input waste. The removal of contaminants and impurities will from the input organic waste 21 to generate the processed input waste 23 will be discussed in greater detail below. The input module 20 allows input of the input organic waste 21 from a waste collection container 22.

In some embodiments, the input module 20 can include a pump/injector to transfer the ground organic waste to the input of the AD tank. In alternative embodiments, the input assembly comprises an auger to transfer the processed input waste 23 to the input of the digester module 30. In some embodiments, the input assembly further includes a grinder hopper which is coupled to the grinder, and a means to lift the container to deposit the organic waste in the container into the grinder hopper, wherein the grinder hopper feeds the input organic waste 21 to the grinder. In some embodiments, the input module 20 further comprises a scale to measure the input of the organic waste from the container into the grinder hopper. Each of the above embodiments will be discussed in greater detail below.

Figure 3:
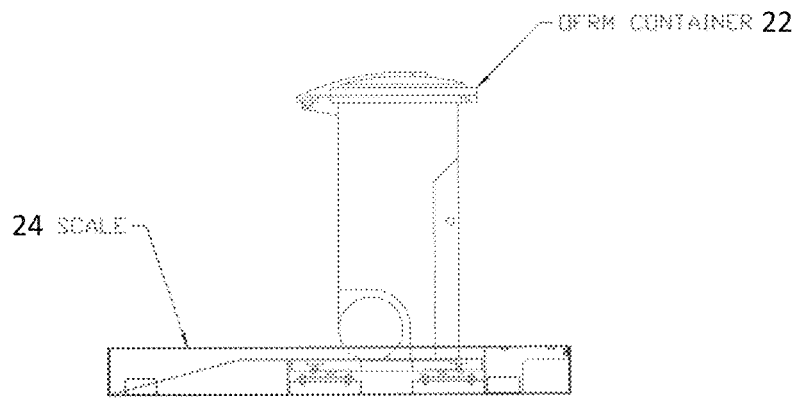
FIG. 3 is a schematic representation of a portion of the input module.

Referring now to FIG. 3, therein is shown a schematic representation of a portion of the input module 20. The input module 20 can include a weight scale 24 to track and control the daily input of the input organic waste 21 into the digester module 30. By tracking the input on a daily, monthly and annual basis, the end user will know exactly how much waste has been diverted from landfill. In some embodiments, the weight scale 24 measures nominal pressure and is a measure of collection of daily input into the digester module 30 by weight.

Figure 4:
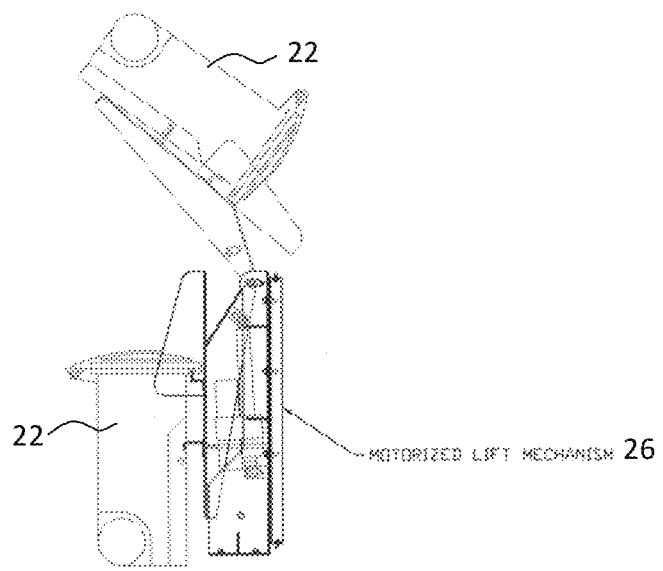
FIG. 4 is an embodiment of the input module.

Reference is made to FIG. 4 showing an embodiment of the input module 20. The input module can include a lifting mechanism 26, e.g., a motorized lift mechanism is configured to deliver or transfer the input organic waste 21 of FIG. 1, including the OFRM, from a container into the Delivery Hopper 28. Accordingly, the motorized lift 26 provides the user with an effortless, hands free loading system to deliver the OFRM into the Delivery Hopper 18. The Delivery Hopper 28 funnels the waste continuously to the Grinder Assembly 29.

Figure 5:
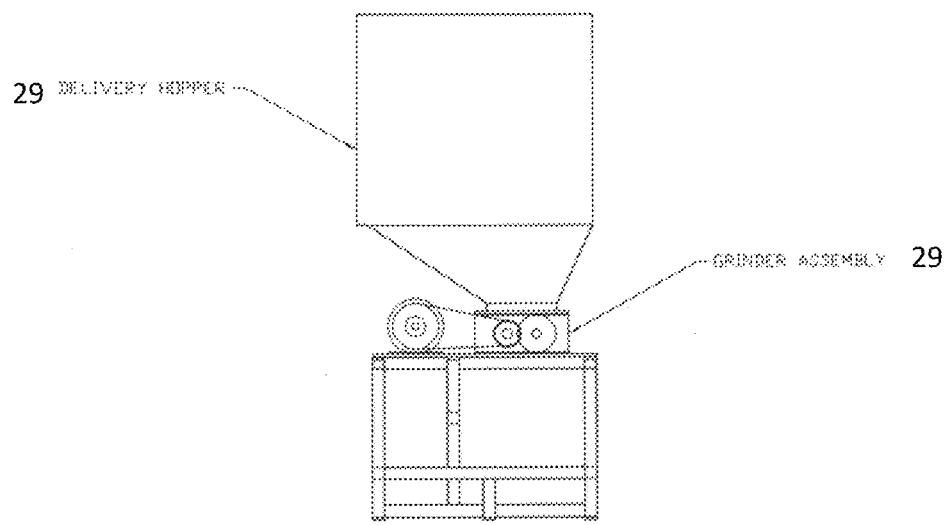
FIGS. 5A and 5B are further embodiments of the input module.
Figure 5:
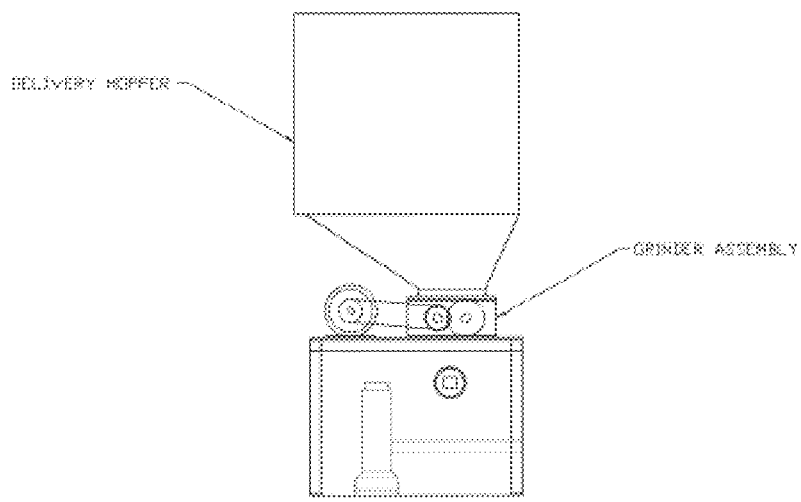

Reference is made to FIGS. 5A and 5B showing further embodiments of the input module 10. The embodiments of the input module 10 can include a Delivery hopper 28 and Grinder Assembly 29, where the outlet of the Delivery Hopper 28, which is connected to the input of the Grinder Assembly 29, holds or store the input organic waste 21 of FIG. 1, including the OFRM, before it enters into the grinder 29. Once the OFRM enters the Hopper 28, it is gravity fed towards a grinder 29, where the grinder 29 comprises cutting or grinding blades. The grinder 29, similar to grinders known in the art, is configured to reduce the size of the OFRM to be digested by the anaerobic microorganisms in the digester module 30 of FIG. 1 to generate the processed input waste 23 of FIG. 2.

In some embodiments, the grinder 29 comprises cutting or grinding blades to reduce the OFRM to a specific particle size for efficient introduction into the digester module 30 and optimum interaction with the anaerobic microbial organisms. By reducing the size of OFRM, the hydrolysis process is optimized by providing more surface area for the microbes to breakdown. In some embodiments, the cutting or grinding blades are custom cutting blades. In some embodiments, the cutting or grinding blades reduce the OFRM to between a range of about ¾ inch to about ¼ inch. The grinder 29 can be configures to have a range of settings available to grind the OFRM to an appropriate size depending on the incoming material.

In some embodiments, the grinder 29 is an in-line macerator. A macerator can breaks up the OFRM, particularly the lignin-containing materials contained therein, so as to facilitate digestion of the OFRM, and to prevent interference with subsequent bio-digestion processes. A macerator encompassed for use in the apparatus, systems and devices herein can be any commercially available macerator. For example, a macerator may use counter-rotating blades that can grind the OFRM. Macerating the OFRM can also be advantageous because breaking up the lignin-containing materials can promote anaerobic digestion of these lignin-containing materials which, prior to maceration, are substantially undigested. Maceration can thereby increase overall biogas output. Such embodiments where the grinder assembly 29 comprises a macerator can be advantageous because the OFRM may contain lignin-containing materials, which can interfere with pumping and subsequent anaerobic bio-digestion processes.

In some embodiments, the Grinding Assembly 29 houses two sets of grinding blades keyed on separate axles with controls to regulate direction and speed. In some embodiments, the cutting or grinding blades in the Grinding Assembly 29 are chain-driven or directly driven by motor. In some embodiments, the motor for driving the grinding blades of the grinding assembly are user controlled, where the operator switches on the motor controlling the grinding assembly at each cycle of the introduction of the OFRM.

The grinder Assembly 29 is designed with a built in safety feature. For example, the safety features will only allow the Grinding Assembly, as well as the cutting or grinding blades, to turn on when the hopper door is completely closed.

As shown in FIG. 5A, in some embodiments, the grinding can be a double stage grinding processes, where located below the Grinding Assembly 29 is an inlet for a pump/injector 45, allowing the processed input waste 23, including ground OFRM, from the grinder 29 to be processed by the pump/injector 45 which is configured to inject the ground OFRM into the input of the Digester module 30. Any pump/injector 45 can be used to force the ground OFRM from the grinder 29 into the inlet of the Digester module 30. A pump/injector 45 encompassed for use herein include any pump/injectors which are known by one of ordinary skill in the art, such as for example, those frequently used in septic systems, which can be configured to directly inject the ground OFRM from the bottom of the grinder assembly into the Digester module 30 under pumped pressure.

Figure 6A:
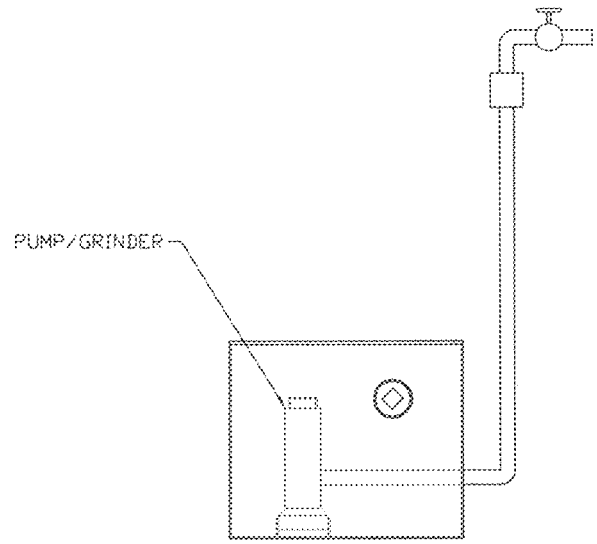
FIGS. 6A and 6B are embodiments of the grinding assembly.
Figure 6B:
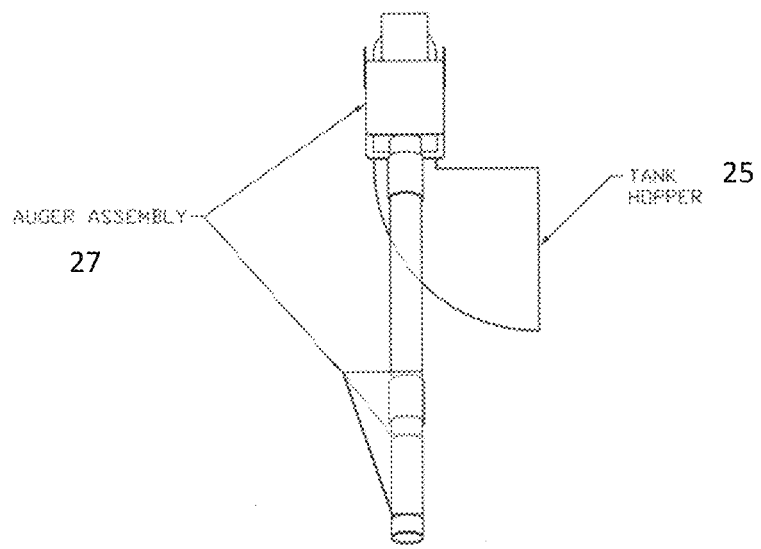

Referring now to FIGS. 6A and 6B, therein is shown embodiments of the grinding assembly 29. As shown in FIG. 6A, the pump/injector 45 to pump the processed input waste 23, including processed or ground OFRM, from a collection area located below the Grinder Assembly 29 to the digester module 30 of FIG. 1. In some embodiments, an inlet of the pump/injector 45 located within the collection area located below the Grinder Assembly 29 to pump the ground OFRM through a pipe and to a pump/injector outlet which is connected to the input of the digester module 30. Located along the pipe is a tap 46 to control the flow of the ground OFRM from the outlet of the pump/injector to the digester module 30. Using a pump/injector 45 to directly feed the ground OFRM into the digester module 30 provides the additional benefit of reducing the retention and/or processing time of the ground OFRM in the digester module 30 due to increased surface area of the OFRM which the anaerobic bacteria can digest.

An alternative implementation of the grinding assembly 29 is shown in FIG. 6B. The grinding assembly 29 can be connected to an Auger Assembly 27. In some embodiments, the processed input waste 23, including the processed or ground OFRM, from the Grinder Assembly 29 drops to a collection area at the bottom of the Grinding Assembly 29 where the proximal end of an Auger Assembly 27 is located. The auger 27, similar to other augers known in the art, can be a closed or open auger, and is configured to convey the ground OFRM from the proximal end to the distal end upon appropriate rotation of the auger along its longitudinal axis, where the distal end is elevated relative to the proximal end. In some embodiments, the auger 27 can be at an angle, e.g., at least about a 45° angle, and in some embodiments, the auger 27 can be vertical. As a result, ground OFRM is generally conveyed out of the grinder assembly 29 and into the input of the tank hopper 25. In some embodiments, the auger 27 works under pressure.

The auger assembly 27 raises ground OFRM from the outlet at the bottom of the Grinder 29 Assembly to the top of the Auger Assembly 27, where the output of the Auger Assembly is connected to the inlet of the Tank Hopper 25. The OFRM exits the Auger assembly 27 from the outlet of the Auger Assembly 27 into the inlet of the tank hopper and to drops into the Tank Hopper 25 by gravity. The bottom of the tank hopper 25 is sloped to a tank hopper outlet which delivers the ground OFRM to an inlet on the digester module 30 below the fluid level present of the digester module 30.

In some embodiments, the grinder assembly 29 is configured to segregate the ground OFRM for additional grinding based on a pre-determined minimum size. For example, segregation can be performed by a segregator which segregated the ground OFRM from large or hard particles. For example, a segregator can comprise a suitably-sized sieve used to retain large or hard particles from the OFRM of a given size while allowing smaller ground OFRM to pass into the next stage of the digestion process, e.g., into the digester module 30.

In other embodiments, segregation by size exclusion can occur by subjecting the ground OFRM to size-limiting aperture or entrance, such that only the smaller-sized or ground OFRM is able to pass into the digester module 30. Larger, released hard particulates of OFRM are not able to pass through, and thus can be deflected or diverted from the OFRM to be digested to another location, thereby segregating the particulates from the OFRM. In some embodiments, ground OFRM can be impelled or otherwise urged towards to the size exclusion structure so that the non-ground OFRM can be re-ground with the grinder 29 or discarded. An exemplary suitable device for such a segregation can use a sieve, or any other structure having one or more size-excluding openings or gaps. Such a structure may have openings that are sized to retain hard particulates having a minimum mean diameter. A suitable mean diameter of the retained particulates can be, for example, greater than 0.25, 0.5, 0.75, 1, 1.5, 2, 3, 4, 5, 8, or 10 centimeters. A preferred mean diameter is about 0.5 centimeters. The desired gap or opening size is also configured not to retain the disrupted waste, thereby allowing the disrupted waste to be passed through the size-excluding structure. Thus the separator may provide a solution to reduce, if not minimize, any problems caused by contaminants, such as non-ground OFRM or hard particles from the OFRM. Contaminant can include, for example, bedding straw, rocks and dirt from the ground, garbage, and other debris.

It is understood that some or all of the metal contaminants may have already been removed from the OFRM during the segregation step, as metal contaminants may share certain properties with hard particulates that would permit their selection and segregation from the disrupted waste. In some embodiments, a magnet may be used to extract ferromagnetic metal contaminants. In some embodiments, the magnet may guide or deflect the metal, so that the metal is retained when the diluted waste is conveyed out or removed from this step, thereby segregating them from the diluted waste.

In some embodiments, the bottom of the Tank Hopper 25 comprises an outlet through which the ground OFRM enters the inlet of the digester module 30. In some embodiments, the Tank Hopper outlet is configured to be connected to a trap, e.g., a U-, S- or J-shaped pipe located below the outlet, such that there always remains a small amount of fluid just after the outlet to create a seal that prevents biogas from the digester module 30 from passing back into the Tank Hopper 25 or the Injector/Grinder Assembly. In some embodiments, the Tank Hopper outlet is connected to a p-trap, which are known by persons of ordinary skill in the art, which comprises an addition of a 90 degree fitting on the outlet side of a U-bend, thereby creating a P-like shape, which are commonly used in plumbing to prevent sewer gasses from backing up. The trap connected to the Tank Hopper outlet is configured to preserve the integrity of the anaerobic environment in the digester module 30.

In some embodiments, the input organic waste 21, including the OFRM, can be diluted in the Tank Hopper 25 to a solid content of about 5%, about 6%, about 7%, about 8%, about 9%, about 10%, about 11%, 12% about 13%, about 15%, about 17%, about 20%, about 25%, about 50%, or any other suitable amount to generate the processed input waste 23. In some embodiments, a solid content is about 12% to 13%. The liquid diluent may be any suitable liquid, such as water. In some embodiments, other liquids, such as complex liquids derived from other processes may be used, or fed back, to act as a diluent. Use of such complex liquids may act as a source of supplemental components or co-substrates to be mixed with the waste. For example, water or fluid digestate from digester assembly 30 can be used as the diluent, or the diluent may be composed in part of the fluid biodigestate. In some embodiments, the addition of the fluid biodigestate to the waste may enhance the subsequent biodigestion of the ORFM, and may also improve the mixing characteristics of the waste.

Referring now to FIG. 7, therein is shown a schematic view of one embodiment of the digester module 30. The single stage anaerobic digester 30 can include a single tank, referred herein to an digester tank 31, which enables anaerobic digestion of the processed input waste 23 to biogas 70 and to a fluid digestate 72, which can be removed as digester effluent 78 to be converted on premises, or off premises to a high quality micronutrient or Effective Microorganism fertilizer.

Accordingly, the present invention comprises a modular system, wherein in some embodiments, the digester module 30 receives the processed input waste 23 from the input module 20, and outputs biogas and fluid digestate to the output module 50, both of FIG. 1.

In some embodiments, the digester module 30 outputs biogas and fluid digestate to output assembly module 50, where the output assembly can be located as part of the facility, e.g., an output assembly can be located underneath, or as part of, the facility. In some embodiments, where the output assembly is part of, or integrated into, the facility, it permits the biogas and fluid digestate to be utilizes by the facility as an energy source for the normal operation of the facility.

In alternative embodiments, the input module 20, digester module 30 and output module 50 are a self-contained system, such the three modules can be installed as a single system at location in a facility, and provided power and water are provided to the system, the system can function independent of other modules at the facility. In such embodiments, the biogas and fluid digestate can also be utilized as an energy source by the facility for the normal operation of the facility.

The digester module 30 can be configured to maintain the temperature and pH at the desired conditions for digestion of the processed input waste 23 by the anaerobic microorganisms, and can include both agitator blades 34 and baffles 33, and heating units 32 for distribution of the processed input waste 23 at a constant temperature and around the digester tank 31. The digester tank 31 can be thermally insulated by a thermal wall 35 for optimal low cost temperature maintained. Both the biogas 70 and the fluid digestate 72 is collected from the digester tank 31 and processed accordingly, where the biogas 70 is filtered clean of contaminating gasses to collect at least about 90% methane gas and the fluid digestate 72 is collected and converted in proprietary manor to a high quality micronutrient or Effective Microorganism (EM), described in further detail below.

Accordingly, one aspect of the present invention relates to a biodigester comprising an anaerobic digestion tank configured to receive ground organic waste, the AD tank comprising: a floor, walls and a ceiling; an inlet for receiving ground organic waste; a plurality of heating units; a plurality of mixers dispersed throughout the AD tank to mix the suspension of solid waste; a plurality of baffles; at least one of or a combination of the following: a plurality of pH sensors, a plurality of temperature sensors, a plurality of pressure sensors, at least one level sensor; at least one biogas outlet for removal of the biogas produced in the AD tank; and at least one fluid digestate outlet for removal of the fluid digestate produced in the AD tank. It is understood that the term "AD tank" and the term "digester tank 31" can be used interchangeably. For example, the Digester tank 31 comprises at least one or a combination of heating units 32, baffles 33 and agitator blades 34 to optimize the anaerobic digestion by a range of microbial organisms present within the tank. As an example, two instances of the baffles 33 can be placed in the digester tank 31 separate the interior of the digester tank 31 into three separate instances of a residence chamber 90.

In some embodiments, the exterior of the digester tank 31 is surrounded by a thermal wall, e.g., a thermal wall that has an insulation value of between R40 and R60, or about R55. In some embodiments, a leak sensor is located between the exterior of the digester tank 31 and the interior of the thermal wall.

In some embodiments, the heating units and/or pressure sensors of the digester tank 31 are embedded within the floors and/or walls of the interior of the digester tank 31. In some embodiments the AD tank temperature sensors, heat units, pressure sensors, leak sensors, agitator blades etc. of the digester tank 31 are connected to a control system which is connected to a computer, the control system couples to the temperature sensors and heating units to provide continuous regulated temperature to the digester tank 31, which are described in greater detail below.

In some embodiments, the plurality of mixers in the digester tank 31 are a plurality of agitator blades. In some embodiments, the digester tank 31 further comprises a plurality of inlets to inject one or more biological additives or a composition comprising anaerobic microorganisms at desired locations in the digester tank 31, which are described in greater detail below.

In some embodiments, the biogas outlet of the AD tank is located near the ceiling of the AD tank to collect biogas produced in the AD tank. In some embodiments, the pressure sensors of the AD tank are located in the top quarter of the AD tank, e.g., in some embodiments, a pressure sensor is located in close proximity to the biogas outlet.

In some embodiments, the floor of the AD tank is sloped towards the fluid digestate outlet, and in some embodiments, the floor of the AD tank further comprises a drain, which can be in close proximity or adjacent to the fluid digestate outlet.

The Digester module 30 as disclosed herein can include a single tank and utilizes a pre-defined range of microbial organisms operating under mesophilic conditions for complete digestion of the processed input waste 23 in a single stage or process. The anaerobic digestion process occurs in the Digester tank 31 which is located within a thermally insulated and sealed system, and comprises; a single OFRM inlet which is connected to the outlet of the tank hopper, an outlet for biogas and an outlet for fluid digestate. The Digester module 30 comprises a single self-contained Digester tank 31, where the AD tank inlet is connected to and receives processed input waste 23 from the air/water outlet of the Tank Hopper 25 of FIG. 2.

The heating units 32 can heat and maintain the fluid digestate 72 to a desired digestion temperature. A variety of different heater unit configurations can be used including, but not limited to, a sleeve heater, an in-line heater or a heater provided within the internal walls of the AD tank. In some embodiments, the heater unit 32 may be integral or separate from the AD Tank. In some embodiments, a heater unit 32 heats the fluid digestate 72 to a temperature in the range from about 30° C. to about 4° C. In some embodiments, the heater unit 32 heats the temperature to about 37° C. In some embodiments, the heating units are located at the bottom of the Digester tank 31, however, they can be positioned elsewhere in the interior of the Digester tank 31 such that they provide a constant heat source for the function of the microbial organisms. In some embodiments, the Digester tank 31 can include heating elements or the heating units 32 embedded within the floor, walls, and optionally ceiling. The heating elements or units 32 may be designed to heat specific zones or regions of the digester. A plurality of temperature sensors 36 may be dispersed throughout the Digester tank 31.

A control system connected to a computer may be coupled to the temperature sensors 36 and the heating elements 32 to provide continuous, regulated heating of the Digester tank 31. In some embodiments, the heating units 32 enable constant temperature of the interior of the Digester tank 31, and are controlled by a feed-back mechanism based on temperature sensors 36 in the interior of the AD tank to ensure that the Digester tank 31 is maintained at a desired and/or constant temperature.

In some embodiments, the temperature of the heating units are controlled by the input to the temperature sensors 36, which measures the internal temperature of the AD tank and controls the heat of the heating units 32 so that the temperature in the internal of the AD tank maintains at a temperature of between about 92° F. to 95° F. In some non-limiting embodiments, the temperature of the interior of Digester tank 31 is regulated to a temperature in the range from about 90° F. to 145° F. In other non-limiting embodiments, the temperature of the AD tank is regulated to a temperature in the range from about 90° F. to 110° F. In still other non-limiting embodiments, the temperature of the AD Tank is regulated to a temperature in the range from about 120° F. to 145° F. In some embodiments, due to the mesophilic nature of the anaerobic microbes used in the digestion as disclosed herein, the heating units are used to maintain a constant temperature of 35° C. to 40° C. A temperature sensor 36 is used to monitor and maintain optimum temperature within the Digester tank 31. In some embodiments, the temperature sensors 36 decrease the temperature of the heating units due to an increase in the internal temperature of the AD tank due to heat derived from an exothermic biological or chemical process of the digestion of the fluid digestate 72.

In some embodiments, the Digester tank 31 comprises at least one heat unit 32, or at least 2, or at least 3, or at least 4 or at least 5 or more heating units. The heating units 32 can be configured to be any conformation and size and can be configured to completely cover at least one surface of the AD tank, or only partially cover a surface of the AD tank. In some embodiments, the Digester tank 31 is surrounded with a thermal wall 35 to maintain the constant temperature of the interior of the Digester tank 31. In some embodiments, the thermal wall 35 has an insulation value of about R55, or an insulation value of between about R40 and R60.

In some embodiments, the Digester tank 31 comprises a plurality of mixers dispersed throughout the AD Tank to mix the suspension of the fluid digestate 72 and digested product. In some embodiments, the mixers are agitator blades 34. In alternative embodiments, non-limiting examples of mixers encompassed for use include peristaltic hose pumps and variable speed mixers. In some embodiments within the scope of the invention, the mixing is slow near the inlet and progressively becomes faster near the outlet. Thus, mixers disposed closest to the AD tank inlet may operate at a slower speed than the mixers disposed closest to the AD tank outlet.

The Digester tank 31 is configured to include elements to mix the fluid digestate 72 within the AD tank. The mixing can take place for a pre-determined amount of time, or until a desired consistency of the fluid digestate 72, or continuously throughout the anaerobic digestion process. In some embodiments, the mixing can occur during the dilution of the fluid digestate 72 or addition of the anaerobic bacteria and microorganisms to the fluid digestate 72 and/or during the addition of other chemical or biological additives as disclosed herein. In some embodiments, the fluid digestate 72 is mixed in the AD tank using agitator blades 34, where the agitator blades rotate about the axis and thereby mix the fluid digestate 72 in the Digester tank 31. In some embodiments, a series of agitator blades 34 in the AD tank are located above the heat source to mix and distribute the fluid and the fluid digestate 72 in the AD tank.

In some embodiments, the Digester tank 31 comprises at least one agitator blade 34, comprising at least one blade, and in some embodiments, the AD tank comprises at least 1, or at least 2, or at least 3, or at least 4, or at least 5, or at least 6 or more agitator blades, each comprising at least 1 blade. In some embodiments, each agitator blade comprises at least 1, or at least 2 or at least 3 or more blades. Each agitator blade is connected to an agitator blade motor 36, which is configured to rotate each agitator blade 34 in Digester tank 31.

In some embodiments, the agitator blade motor 36 is located external to the thermal wall 36 of the AD tank. The agitator blades 34 can rotate in the same direction or in opposite directions with respect to each other. In some embodiments, the agitator blades 34 rotate at the same speed with respect to each other, and in some embodiments, they rotate at different speeds with respect to each other. In some embodiments, the agitator blades rotate at about 2-10 RPM, or about 2-4 RPM, or about 4-6 RPM, or about 6-8 RPM, or about 8-10 RPM or in the range of about 10-20 RPM or faster than 20 RPM. In some embodiments, the agitator blades 34 rotate at about 6 RPM.

The digester module 30 can include baffles 33 affixed within the digester tank 31. In some embodiments, to improve mixing of the fluid digestate 72 in the AD tank, the AD tanks comprise a plurality of deflecting plates or baffles 33 disposed within and/or along the walls of the AD tank. In some embodiments, the deflecting plates and/or baffles 33 have a surface that provide points of attachment for the anaerobic bacteria and microorganisms. In some embodiments, the AD tank comprises at least one baffle 33, where the baffle 33 is configured to regulate the flow of a fluid in the AD tank. In some embodiments, the baffle 33 includes at least one baffle board or baffle plate. In some embodiments, a series of baffles 33 in the AD tank are located between the agitator blades to regulate and distribute the flow of the OFRM in the AD tank. In some embodiments, the Digester tank 31 comprises at least one baffle 33, comprising at least one baffle board, and in some embodiments, the AD tank comprises at least 1, or at least 2, or at least 3, or at least 4, or at least 5, or at least 6 or more baffles, each comprising at least 1 baffle board. In some embodiments, each baffle comprises at least 1, or at least 2 or at least 3 or more baffle boards.

In some embodiments, the baffle 3 can be oriented vertically, spanning from the top of the digester tank 31 to the bottom 31 of the digester tank 31. For illustrative purposes, FIG. 7 depicts the digester tank 31 with the baffle 33 without a flow space, which is a space between the top of the digester tank 31 to the bottom 31 of the digester tank 31, although it is understood that the baffle 33 can be configured within the digester tank 31 differently. For example, the baffle 33 can include the flow space in the portion of adjacent the top or ceiling of the digester tank 31, the bottom or floor of the digester tank 31, or a combination thereof. The flow space in the baffle 33 can allow the fluid digestate 72 and solids to flow through the digester tank 31.

As a further example, the gap or space in the baffle 33 can vary relatively from one instance of the baffle 33 to then next instance of the baffle 33. As a specific example, the flow space in the baffle 33 closest to the inlet of the digest tank 31 can be greater than the flow space in the baffle 33 closest to the fluid digestate outlet 44.

In yet a further example, the flow space in the baffle 33 can be dynamically adjusted. More specifically, mechanical means, such as hydraulically actuated gates integrated with or attached to the baffle 33 or along the walls, top, or bottom of the digester tank 33 can adjust the dimensions of the flow space.

The AD tank may comprise a plurality of chemical inlets 41 to inject one or more chemical or biological additives at desired locations within the AD tank. Non-limiting examples of such additives include acids or bases for pH control, microbial inoculum, nutrients to support microbial growth, defoaming and/or antifoaming agents, water, and so forth. Some non-limiting examples of nutrients which support microbial growth include free amino acid nitrogen, surfactants, metals cations such as calcium, zinc, copper, and so forth. Certain metal cations may also be added to facilitate enzyme activity and to provide "food", along with the amino acids, for microbial growth. In some embodiments, an additive is a carbon-rich waste product, or a nitrogen-rich waste product, or one or more enzymes to increase digestion of poorly-digestible components, such enzymes including but are not limited to, cellulase, hemicellulase, and lipase, proteinases, liginases, laccases, ureases. In some embodiments, the chemical inlets may be configured as a liquid spray system disposed at the ceiling.

The apparatus for the AD tank within the scope of the present invention may include other features to improve the yield, efficiency, and performance of the AD tank to digest the fluid digestate 72. As disclosed herein, the AD Tank comprises a combination of sensors for monitoring and control of the AD process. In some embodiments, the AD tank comprises a range of sensors, including for example, at least one pH sensor 37, at least one gas leak sensor 38, at least one level sensor 39, at least one temperature sensor 36, at least one biogas pressure sensor 40.

The temperature sensor 36 measures the internal temperature of the AD tank and maintains the temperature to between 92° F. to 95° F. The pH sensor 37 monitors the pH in the interior of the AD tank, in particular the fluid being digested, and maintains a pH level of 6-7. The level sensors 39 detect the level of the fluid digestate 72 in the AD tank and once the material reaches the level sensor, a pump 53 and gate valve is activated and the fluid digestate evacuated to the reservoir tank 51 for a predetermined time period. The pressure sensor 40 measures the pressure of the biogas 70 in the AD tank, and once the level of gas reaches to about 3 PSI, the gas compressor 59 is activated and the biogas is evacuated via the biogas outlet 42 to the biogas line 43 for a predetermined time period. The gas leak detector 38, detects abnormally high levels of gases outside the Digester tank 31 and between the thermal wall 35 or immediately surrounding the thermal wall 35 of the AD tank assembly 30.

Accordingly, various gas, temperature, pH, fluid levels, pressure and flow sensors are attached in numerous strategic places in the Digester tank 31 and other regions of the BioVessel 10 system as disclosed herein to gather continual data and regulate processes. Systems and methods for gathering and aggregating data about the process interact with all processes of this invention.

In some embodiments, the plurality of pH sensors in the digester tank 31 are coupled to a control system, wherein the control system is connected to a computer, the pH sensors detecting the pH of the suspension of organic waste in the digester tank 31. In some embodiments, the pH sensors maintain the pH of the organic waste or the processed input waste 23 being converted to the fluid digestate 72 in the digester tank 31 to between pH of 6-7.

In some embodiments, a plurality of chemical inlets 41 are preferably coupled to the control system and introduce acid or base to the suspension of organic waste to control the pH based upon pH measurements from the pH sensors. In a typical AD tank digestion process, the pH is preferably maintained in the range from about pH 5 to pH 9. In some embodiments, a pH sensor is used to maintain the optimum pH level of 6.5 to 7. The actual pH may vary depending upon the source of waste solid and the type of OFRM. As an example, animal waste digestion may operate at a pH range from about 7.1 to 7.6, for corn ethanol solids, the pH may range around 5.2, and for cane solids the pH may range around 6 or slightly higher. An important benefit of this pH control system is the ability to monitor and control pH within various regions of the AD tank in real time. Prior art pH control techniques require days and sometimes weeks to control pH conditions within the AD tank.

Other sensors may be dispersed throughout the AD tank as needed and coupled to the control system to monitor the AD tank operation and make appropriate changes to AD tank operation, such as addition of appropriate chemical or biological additives, including increased addition of a range of different anaerobic microorganisms as disclosed herein.

The size of the Digester tank 31 is crucial to insure complete digestion of the fluid digestate 72. The daily input capacity is directly correlated to the size of the Digester tank 31. The ratio of AD tank size to daily input is 30:1. Inside the Digester tank 31, fluid digestate 72 is acted upon by a microbial signature, without manure or fecal matter, which creates biogas and promotes microbial degradation of the fluid digestate 72 into the digester effluent 78 and the biogas 70.

Accordingly, the Digester tank 31 as disclosed herein allows for scalability of daily inputs from a range of about 100 lbs. to about 10000 lbs. In some embodiments, the volume of input into the AD tank is between about 100-200 lb, or about 200-300 lb, or about 300-500 lb, or about 500-750 lb, or about 750-1000 lb, or about 1000-2000 lb, or about 2000-3000 lb, or about 3000-4000 lb, or about 4000-5000 lb, or about 5000-6000 lb, or about 6000-7000 lb, or about 7000-8000 lb or about 8000-9000 lb, or about 9000-10000 lb or more than about 10000 lb. Additionally, the type of the processed input waste 23 into the Digester tank 31 can also range from 5% to 100% moisture content while maintaining peak methane production capabilities. In some embodiments, optimized feedstock for the machine consists of food scraps known as Organic Food Resource Material. In some embodiments, the interior of the AD tank is sized to provide adequate anaerobic digestion and time of the OFRM. The Digester tank 31 may have a volume equivalent selected to provide a retention time in a range of about approx. 8 hours to about 48 hours based on the flow rate of the ground OFRM into the Digester tank 31.

In some embodiments, the Digester tank 31 comprises a plurality of pressure sensors 40 located in the upper fourth, or near the top of the AD tank. These pressure sensors 40 can be located on the sides of the interior of the AD tank and/or on the ceiling of the Digester tank 31. As biogas is produced from the digestion of the OFRM continuously flows upward within the Digester tank 31, once the pressure builds to a desired and pre-defined set point, a pressure sensor 40 triggers the opening of a biogas outlet 42 located at, or near the top of the Digester tank 31 to efflux the biogas to an inlet of a biogas line 43 which is connected to the output assembly 50 to deliver the biogas to the output assembly 50 for filtration. In some embodiments, the biogas line 43 comprises at least one gas flow sensor and/or gas analyzer to measure the flow and quality of the effluxed biogas from the AD tank for levels of a variety of gasses, including but not limited to, $CH_4$, $H_2S$, $CO_2$ and $O_2$. The data collected is sent to the on board CPU for processing.

The digestate fluid can be removed from the Digester tank 31 to the output assembly by a number of ways. In some embodiments, the Digester tank 31 also comprises a digestate fluid outlet 44. In some embodiments, the digestate fluid outlet 44 is located in the floor of the AD tank to drain the digestate fluid from the Digester tank 31. In some embodiments, the floor of the AD tank is preferably sloped towards the digestate fluid outlet 44 to facilitate drainage out of the digestate fluid outlet 44. The slope may be from 1% to 2%, front to back along the entire AD tank floor, or to the middle of the floor of the AD tank. In some embodiments, the digestate fluid outlet 44 is connected to a reservoir storage tank 51 in the output assembly 50 for storage of the digestate fluid. The digestate is conveyed to the reservoir storage tank 51 by any device which is configured or suitable for conveying liquidified or semi-solid material. In some embodiments, the fluid digestate is conveyed through pipes using a passive conveyance or by active conveyance, or any suitable combination thereof. In some embodiments, the fluid digestate is conveyed to the reservoir storage tank 51 using a pump 53.

In some embodiments, floor of the Digester tank 31 also comprises a drain located adjacent or next to the fluid digestate outlet 44, where the drain is coupled with the ability to a drainage system, where the AD tank has the ability to introduce clean water into the AD tank, thus enabling the entire AD tank to be flushed and drained. A suitable valve plugs the drain when not in use. In some embodiments, clean water can be flushed through the AD tank using a spray system, all water directed to the areas in the Digester tank 31 that require cleaning and flushing. This is important in circumstances where the entire content of the AD tank needs to be flushed and replaced. In some embodiments, the AD tank can be cleaned out in less than 12 hours, beginning to end. This is a huge advantage than removing the top of the AD tank to clean. If the digester is providing either electricity or has, the entire down time can be limited to 24 hours and therefore saves money from penalties for down time due to cleaning due to non-production of gas or electricity.

In some embodiments, the fluid digestate 72 can be removed from the Digester tank 31 continuously, which can reduce down time, and in some embodiments the fluid digestate 72 is removed from the AD tank in batched after a pre-defined period of anaerobic digestion in the Digester tank 31, which can allow for more thorough digestion and/or complete mixing of the processed input waste 23.

The digester unit 30 can include a digester process solution 74. The digester process solution 74 can be mixed or combine with the processed input waste 23 in the digester tank 31. The digester process solution 74 is a specific bacterial component that includes a combination of at least one species each of a hydrolytic bacteria, acidogenic bacteria, acetogenic bacteria, methanogenic bacteria, or a combination thereof. The digester process solution 74 can be introduced to the digester tank 31 to releases the nutritional and energy elements of the processed input waste 23.

The Digester tank 31 may be seeded with the microorganisms, or the microorganisms may be carried into the Digester tank 31 as a component of the processed input waste 23. The microorganisms convert solids in the processed input waste 23 into, among other things, the biogas 70 and the fluid digestate 72 which is collected and removed from the Digester tank 31.

Although a preferred embodiment of the present invention utilizes anaerobic digestion in the digester tank 31 and it will be described in this context, it is also applicable to aerobic digestion or a combination in sequence of aerobic and anaerobic digestion. In some embodiments, the digester tank 31 can include a solution with numerous psychrophilic, mesophilic and thermophilic bacteria families of the Archaea general, which are useful in anaerobic digestion.

In some embodiments, an anaerobic microorganism encompassed for use in the present invention is a fermentative bacteria in the processing of thermophilic waste sludge is the *Thermoanaerobacterium* genus. An example is the species aotearoense of the Clostridia class. For aerobic digestion major bacterial groups in the beginning of the composting process are mesophilic organic acid producing bacteria such as *Lactobacillus* spp. and *Acetobacter* spp. Later, at the thermophilic stage, Gram-positive bacteria such as *Bacillus* spp. and Actinobacteria, become dominant. The processed input waste 23 and other feedstock commonly contains biological solids that are both digested through anaerobic and aerobic digestion as well as solids that require extensive treatment and retention times or even cannot be successfully processed.

Methanogenesis or biomethanation is the formation of methane by microbes known as methanogens. Organisms capable of producing methane have been identified only from the domain Archaea, a group phylogenetically distinct from both eukaryotes and bacteria, although many live in close association with anaerobic bacteria. Methanogens are microorganisms that produce methane as a metabolic byproduct in anoxic conditions. They are classified as archaea, a domain quite distinct from bacteria.

Exemplary examples of methogens, or methanogenic bacteria included in the digester process solution 74, which can be used in the anaerobic digestion process in the methods, systems and apparatus as disclosed herein include, but are not limited to: *Methanobacterium bryantii, Methanobacterium formicium, Methanobrevibacterium arboriphilus, Methanobrevibacter gottschalkii, Methanobrevibacterium ruminantium, Methanobrevibacter smithii, Methanocalculus chunghsingensis, Methanococcoides burtonii, Methanococcus aeolicus, Methanococcus deltae, Methanococcus jannaschii, Methanococcus maripaludis, Methanococcus vannielli, Met hanocorpusculum labreanum, Methanoculleus bourgensis, Methanoculleus marisnigri, Methanofollis liminatans, Methanogenium cariaci, Methanogenium frigidum, Methanogenium organophilum, Methanogenium wolfei, Methanomicrobium mobile, Methanopyrus kandleri, Methanoregula boonei, Methanotrix concilli, Methanosaeta thermophile, Methanosarcina acetivorans, Methanosarcina barkeri, Methanosarcina mazei, Methanosphaera stadtmanae, Methanospirillium hungatei, Methanothermobacter defluvii, Methanothermobacter thermautotrophicus, Methanothermobacter thermoflexus, Methanothermobacter wolfei, Methanothrix sochngenii.*

In some embodiments, the digester process solution 74 can include composition comprising a combination of methogenic bacteria and anaerobic bacteria are used in the anaerobic digestion of the processed input waste 23 according to the methods and systems as disclosed herein. In some embodiments, the digester process solution 74 can include at least about 3, or at least about 4, or at least about 5, or at least about 6, or at least about 7, or at least about 8, or at least about 9, or at least about 10, or at least about 10-12, or at least about 12-15, or at least about 15-20 or more than 20 methogenic bacteria in the anaerobic digestion of the digester process solution 74 in the digester tank 31 according to the methods and systems as disclosed herein. As a specific example, the digester process solution 74 can preferably include methanogenic bacteria of *methanotrix concilli, methanosarcinar barkeri, methanosarcinar mazei, methanospirillum hungatei, mehtanococcus vannielli, methanobacterium formicium, methanobrevibacterium ruminantium, methanobacterium arboriphilus*, or a combination thereof.

The fluid digestate 72 in the digester tank 31 can be removed as digester effluent 78 after a residence period 76. The residence period 76 is a predetermined period sufficient for conversion of the processed input waste 23 into the biogas 70 and raw material for a high quality micronutrient or effective microorganism solution. For example, the residence period 76 can be a period of time ranging from about 10 days to 60 days. In another example, the residence period 76 can be a period ranging from 20 to 40 days. In a further example, the residence period 76 can be a period ranging from 25 to 30 days.

Referring now to FIG. 8, therein is shown a schematic representation of the output module 50. In some embodiments, the output module 50 can include a distillate fluid processing apparatus 52 and a biogas processing apparatus 55. In some embodiments, the biogas 70 can be filtered by the biogas processing apparatus 55 to remove $H_2O$, $CO_2$ and $H_2S$, and where the filtered biogas 70 as methane and can be stored in a gas storage tank. In some embodiments, the residence period 76 can be the time for the digested organic waste to reach a pre-defined level in the air-tight chamber.

Referring now to FIG. 9, therein is shown a schematic representation of an embodiment of the distillate fluid processing apparatus 52. The distillate fluid processing apparatus 52 can include a reservoir tank 51, a pump 53, and a liquid flow sensor 54. The fluid distillate outlet 44 in the digester tank 31 of FIG. 7 is connected to the reservoir tank 51 via a series of tubes or other connectors, and located in the connection between the fluid distillate outlet 44 and the reservoir tank 51 is at least one pump 53 to pump the digester effluent 78 into the reservoir tank 51, and at least one liquid flow sensor 54 to monitor the flow rate and the amount of the digester effluent 78 pumped into the reservoir tank 51. The liquid flow sensor 54 measures the amount of digester effluent 78 evacuated from Digester tank 31 to reservoir storage tank 51.

The pump 53 can be any mechanical pump, and in some embodiments is a filtered pump system which can be electronically activated and monitored to pump digester effluent 78 from the digester tank 31 into the reservoir tank 51. The reservoir tank 51 stores the digester effluent 78 so it can be used as a pathogen free digestate which can be utilized as a fertilizer, soil amendment or conditioner or for other uses.

In some embodiments, the digester effluent 78 is converted in proprietary manor to an enriched effective microorganism solution 80, which is a high quality micronutrient or effective microorganism solution, with an effluent enhancement solution 82. The effluent enhancement solution 82 is a combination of microorganisms for removing pathogens and refining the digestate effluent. For example, the effluent enhancement solution 82 can include hydrolytic bacteria, lactic acid bacteria, yeast, phototropic bacteria, or a combination thereof.

In some embodiments, the reservoir tank 51 is a 100-gallon NSF approved tank. Through a series of valves the same pump 53 can be used to evacuate this reservoir tank. In some embodiments, there is an outlet in the reservoir tank 51 which for efflux or collection of any of the biogas 70 released from the digester effluent 78, which is connected to the biogas line 44 prior to the biogas filters 56 to be processed by the biogas processing apparatus 55.

Upon anaerobic digestion of the OFRM, the biogas 70 and a portion of the fluid digestate 72 is also produced. The fluid digestate 72 can include at least partially nutrient-depleted media resulting from anaerobic bacterial growth, as well as the bacteria. The fluid digestate 72 can include other volatile and non-volatile metabolites from bacteria growth. The solid content of fluid digestate 72 can vary, depending on the extent of digestion, the initial moisture/solid content of the waste, and the amount of water added to or removed from the Digester tank 31 during the digestion.

Referring now to FIG. 10, therein is shown a schematic view of an embodiment of the biogas processing apparatus 55. The biogas processing apparatus 55 can include a plurality of biogas filters 56, at least one gas flow sensor 57, at least one gas flow analyzer 58, at least one gas compressor 59, and at least one gas storage tank 60 tank). The biogas line 43 transports the biogas 70 from the biogas outlet 42 in the Digester tank 31 to the biogas storage tanks 60. Located along the biogas line 43, between the biogas outlet 42 and the biogas storage tanks 60, are at least one biogas filter 56, at least one gas flow sensor 57, at least one gas flow analyzer 58, and at least one gas compressor 59.

The biogas filter 56 removes contaminating biogases e.g., filters the biogas free of specific gasses types, e.g., but not limited to $H_2O$, $CO_2$ and $H_2S$. Any gas filters can be used as the biogas filters 56, for example, but not limited to commercially available filters such as Shelco Filters.

The biogas 70 can include one or more inert gases, or gases produced by anaerobic digestion such as methane, carbon dioxide, or nitrogen. For example, waste gases left after enriching the biogas 70, primarily carbon dioxide, can be used for bubble scouring in the biogas filters 56. Preferably, the biogas filters 56 are operated in a sealed tank with gases used for scouring bubbles captured in a head space of the tank and recycled to the aerators. In some embodiments, the biogas filters 56 can capture certain gasses, e.g., $CO_2$ for reuse, and in such embodiments, the collected $CO_2$ biogas is delivered via gas lines to a $CO_2$ storage tank and/or to be used directly on site.

The gas flow sensor 57 detects the rate of flow of the biogas in the biogas line 43, and the gas flow analyzer 58 detects the purity and quality of the biogas 70 remaining, in particular, the quality of the methane gas and removal of contaminant gasses $CO_2$, $H_2S$ and $O_2$. Also present in the biogas line is a gas totalizer which measures the total volume of gas produced.

The biogas 70 remaining after processing, typically at least 90% methane is compressed with the gas compressor 59 to, for example, at least about 3600 psi and is stored in a plurality of biogas storage tanks 60. In some embodiments, the biogas processing apparatus 55 can include at least three compressed natural gas or alternatively four Gallon gasoline equivalent tanks as the biogas storage tanks 60. Alternatively, the biogas can be diverted from being stored in the storage tanks and used directly on site as a natural gas supplement.

The resulting method, process, apparatus, device, product, and/or system is straightforward, cost-effective, uncomplicated, highly versatile, accurate, sensitive, and effective, and can be implemented by adapting known components for ready, efficient, and economical manufacturing, application, and utilization. Another important aspect of an embodiment of the present invention is that it valuably supports and services the historical trend of reducing costs, simplifying systems, and increasing performance.

These and other valuable aspects of an embodiment of the present invention consequently further the state of the technology to at least the next level.

While the invention has been described in conjunction with a specific best mode, it is to be understood that many alternatives, modifications, and variations will be apparent to those skilled in the art in light of the aforegoing description. Accordingly, it is intended to embrace all such alternatives, modifications, and variations that fall within the scope of the included claims. All matters set forth herein or shown in the accompanying drawings are to be interpreted in an illustrative and non-limiting sense.

What is claimed is:

1. A waste processing system comprising:
an input module for converting input organic waste into processed input waste;
a digester module, coupled to the input module, for generating biogas and digester effluent from the processed input waste, including:
a digester tank;
baffles affixed within the digester tank;
digester process solution in the digester tank including, hydrolytic bacteria, acidogenic bacteria, acetogenic bacteria, methanogenic bacteria, or a combination thereof, for converting the processed input waste into the biogas and the digester effluent;
an output module, coupled to the digester module, for collecting the biogas and digester effluent after a residence period; and
an distillate fluid processing apparatus, coupled to the output module, for processing the digester effluent with an effluent enhancement solution to generate an enriched effective microorganism solution.

2. The system as claimed in claim 1 wherein the effluent enhancement solution includes hydrolytic bacteria, lactic acid bacteria, yeast, phototropic bacteria, or a combination thereof.

3. The system as claimed in claim 1 further comprising agitators in the digester tank for mixing a fluid digestate in the digester tank.

4. The system as claimed in claim 1 wherein the input module is directly connected to the digester module.

5. The system as claimed in claim 1 wherein the digester module is directly connected to the output module.

6. A method of operation of a waste processing system comprising: processing input organic waste to generate processed input waste:

combining the processed input waste with a digester process solution in a digester module to generate biogas and fluid digestate, the digester process solution includes hydrolytic bacteria, acidogenic bacteria, acetogenic bacteria, methanogenic bacteria, or a combination thereof;

collecting the biogas: and generating digester effluent at a solids content of about 10% from the fluid digestate based on a residence period, further comprising processing the biogas to remove impurities, further comprising combining the digester effluent with an effluent enhancement solution to generate an emiched effective microorganism solution, the effluent enhancement solution includes hydrolytic bacteria, acidogenic bacteria, acetogenic bacteria, methanogenic bacteria, or a combination thereof.

* * * * *